United States Patent
Bastide et al.

(10) Patent No.: US 10,687,764 B2
(45) Date of Patent: Jun. 23, 2020

(54) BIOMARKER CHANGE INDICATOR FOR BEHAVIORAL HEALTH

(71) Applicant: International Business Machines Corporation, Armonk, NY (US)

(72) Inventors: Paul R. Bastide, Boxford, MA (US); Liam S. Harpur, Skerries (IE); Lin Sun, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/408,511

(22) Filed: May 10, 2019

(65) Prior Publication Data

US 2019/0261929 A1    Aug. 29, 2019

Related U.S. Application Data

(63) Continuation of application No. 15/813,250, filed on Nov. 15, 2017.

(51) Int. Cl.
  *A61B 5/00*  (2006.01)
  *G16H 50/30*  (2018.01)
  (Continued)

(52) U.S. Cl.
  CPC ............ *A61B 5/747* (2013.01); *A61B 5/0022* (2013.01); *A61B 5/486* (2013.01); *G06F 16/436* (2019.01);
  (Continued)

(58) Field of Classification Search
  CPC ....... A61B 5/747; A61B 5/0022; A61B 5/486; G16H 50/30; G16H 10/65; G06F 16/436; G06F 16/637; G06F 16/437; G16B 50/00
  See application file for complete search history.

(56) References Cited

U.S. PATENT DOCUMENTS

2010/0273610 A1  10/2010 Johnson
2015/0297109 A1* 10/2015 Garten ............... A61B 5/04845
                                                          600/544
(Continued)

OTHER PUBLICATIONS

"Annual Total Direct and Indirect Costs of Serious Mental Illness (2002)", National Institutes of Health, <https://www.nimh.nih.gov/health/statistics/cost/index.shtml>, 1 page.
"Biomarker", Wikipedia, The free Encyclopedia, <https://en.wikipedia.org/wiki/Biomarker>, This page was last edited on Jul. 30, 2017, 5 pages.

(Continued)

*Primary Examiner* — Amine Benlagsir
(74) *Attorney, Agent, or Firm* — Joseph P. Curcuru; Gilbert Harmon, Jr.

(57) ABSTRACT

Embodiments describing an approach for detecting user biomarker identifier changes based on audio preferences and generating biometric alerts based on the detected biomarker identifier changes. Receiving a user's current audio preferences. Retrieving the user's historic audio preferences and biometric data associated with the user's historic audio preferences. Analyzing the user's current audio preferences based on the user's historic audio preferences and the biometric data associated with the historic audio preferences. Creating a user biometric profile based on analyzing the user's current audio preferences, the user's historic audio preferences and the biometric data associated with the user's historic audio preferences; and outputting the user biometric profile.

7 Claims, 4 Drawing Sheets

(51) Int. Cl.
  *G16H 10/65* (2018.01)
  *G06F 16/435* (2019.01)
  *G06F 16/635* (2019.01)
  *G16B 50/00* (2019.01)

(52) U.S. Cl.
  CPC .......... *G06F 16/437* (2019.01); *G06F 16/637* (2019.01); *G16B 50/00* (2019.02); *G16H 10/65* (2018.01); *G16H 50/30* (2018.01)

(56) References Cited

U.S. PATENT DOCUMENTS

| | | | |
|---|---|---|---|
| 2016/0055420 A1* | 2/2016 | Karanam | G16H 50/20 700/52 |
| 2016/0086089 A1 | 3/2016 | Ritchie | |
| 2016/0179460 A1* | 6/2016 | MacDonald | G06F 3/165 381/107 |

OTHER PUBLICATIONS

"Mental Health: Research Findings", AHRQ, U.S. Department of Health & Human Services, Content last reviewed Oct. 2014. Agency for Healthcare Research and Quality, Rockville, MD., <http://www.ahrq.gov/research/findings/factsheets/mental/mentalhth/index.html>, 10 pages.

Bastide et al., "Biomarker Change Indicator for Behavioral Health", U.S. Appl. No. 15/813,250, filed Nov. 15, 2017, 31 pages.

Boksa, Patricia, "A way forward for research on biomarkers for psychiatric disorders", J Psychiatry Neurosci. Mar. 2013; 38(2): 75-77. doi: 10.1503/jpn.130018, 4 pages.

Goodman, Wayne, K., "Research on Biomarkers for Mental Disorders", National Institute of Mental Health, NAMHC Concept Clearance • Feb. 13, 2009, <https://www.nimh.nih.gov/funding/grant-writing-and-application-process/concept-clearances/2009/research-on-biomarkers-for-mental-disorders.shtml>, 2 pages.

IBM Appendix P, list of patents or applications treated as related, filed herewith, 2 pages.

* cited by examiner

BIOMARKER CHANGE INDICATOR FOR BEHAVIORAL HEALTH

BACKGROUND OF THE INVENTION

The present invention relates generally to the field of biometric monitoring, and more particularly to measure, analyze, monitor, and/or record biometric and/or biomarker changes in a user.

Many people listen to music while they are working, exercising, driving, doing homework etc. Having the right music playing during a particular activity is often key to the user's happiness and success for that activity, and can be used to monitor a user's health by monitoring biometric identifiers. Biometric identifiers are the distinctive, measurable characteristics used to label and describe individuals. Biometric identifiers (i.e., biometric data) are often categorized as physiological versus behavioral characteristics. Physiological characteristics are related to the shape of the body. Examples include, but are not limited to fingerprint, palm veins, face recognition, DNA, palm print, hand geometry, iris recognition, retina and odor/scent. Behavioral characteristics are related to the pattern of behavior of a person, including but not limited to typing rhythm, gait, and voice.

These biometric identifiers are often used as biomarkers indicative of a presence of disease/infection or specific environmental exposure. Biometric identifiers are a valuable indicator for health issues, including mental health issues, yet many individuals do not use biometric capable devices to record biometric feed/data. Predictions for 2017 include an estimated 200 million biometric capable devices will be sold. Creating a clear need to passively acquire biometric identifiers to capture key biometric data and change healthcare monitoring, and need to better detect biomarker changes in order to intervene with behavioral and/or overall health.

SUMMARY

Embodiments of the present invention disclose a method, a computer program product, and a system for biomarker identifier changes. A method for detecting user biomarker identifier changes based on audio preferences and generating biometric alerts based on the detected biomarker identifier changes, the method includes receiving, by one or more processors, a user's current audio preferences. Retrieving, by the one or more processors, the user's historic audio preferences and biometric data associated with the user's historic audio preferences. Analyzing, by the one or more processors, the user's current audio preferences based on the user's historic audio preferences and the biometric data associated with the historic audio preferences. Creating, by the one or more processors, a user biometric profile based on analyzing the user's current audio preferences, the user's historic audio preferences and the biometric data associated with the user's historic audio preferences, and outputting, by the one or more processors, the user biometric profile.

A computer program product for detecting user biomarker identifier changes based on audio preferences and generating biometric alerts based on the detected biomarker identifier changes, the computer program product includes one or more computer readable storage devices and program instructions stored on the one or more computer readable storage devices, the stored program instructions comprising, program instructions to receive a user's current audio preferences. Program instructions to retrieve the user's historic audio preferences and biometric data associated with the user's historic audio preferences. Program instructions to analyze the user's current audio preferences based on the user's historic audio preferences and the biometric data associated with the historic audio preferences. Program instructions to create a user biometric profile based on analyzing the user's current audio preferences, the user's historic audio preferences and the biometric data associated with the user's historic audio preferences, and program instructions to output the user biometric profile.

A computer system for detecting user biomarker identifier changes based on audio preferences and generating biometric alerts based on the detected biomarker identifier changes, the computer system includes one or more computer processors, one or more computer readable storage devices, program instructions stored on the one or more computer readable storage devices for execution by at least one of the one or more computer processors, the stored program instructions comprising, program instructions to receive a user's current audio preferences. Program instructions to retrieve the user's historic audio preferences and biometric data associated with the user's historic audio preferences. Program instructions to analyze the user's current audio preferences based on the user's historic audio preferences and the biometric data associated with the historic audio preferences. Program instructions to create a user biometric profile based on analyzing the user's current audio preferences, the user's historic audio preferences and the biometric data associated with the user's historic audio preferences, and program instructions to output the user biometric profile.

DETAILED DESCRIPTION

Figure 1:
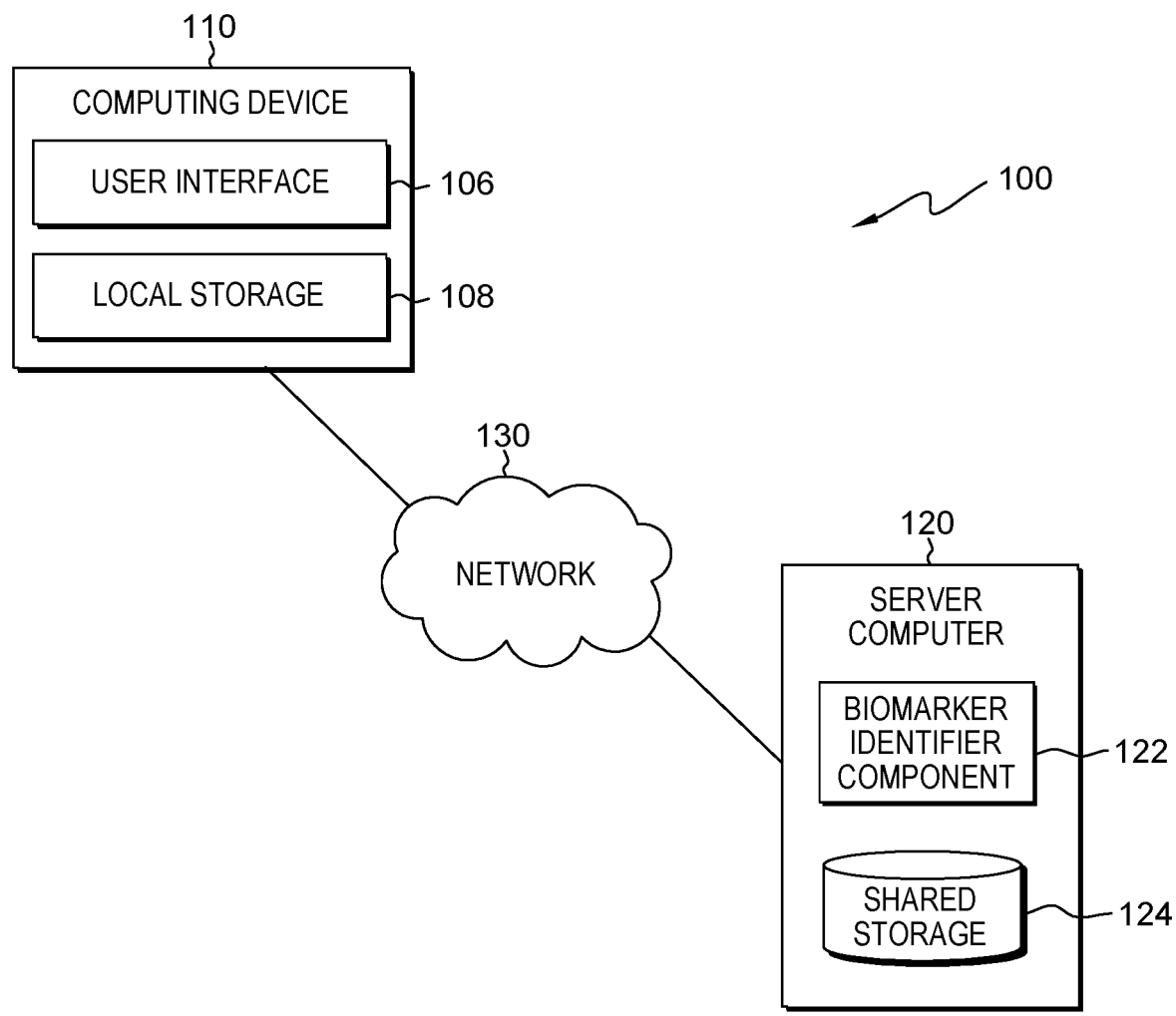
FIG. 1 is a functional block diagram illustrating a distributed data processing environment, in accordance with an embodiment of the present invention.

Embodiments of the current invention leverages the music played by the device currently to determine the user's biometric information. Embodiments of the current invention can source user's biometric information (approximate or exact or relative affect) from music that the user played or is currently playing, based on previously sourced biometric information from biometric capable devices while a user plays music. For example, a smart watch that records a user's biometric identifiers and/or vitals while the user exercises. The music monitored can be current music playing or historical music playing to cover a good range of user's biometric information for further interesting analysis of user's biometric information. Embodiments of the present invention can also focus on segment of music rather than an entire musical track. Embodiments of the current invention normalize on music satisfaction (e.g. a user fast forwarded so they must be annoyed by music more than amplifying or reflecting the music's pattern). Embodiments of the current invention can isolate the music based on region or demographic background (i.e., age, gender, region, etc.) or medical background. The biometric data can be a relative indicator versus a real indicator. Embodiments of the current invention improve the field of user biometric and user biomarker monitoring, analysis, and recording.

Embodiments of the present invention are capable of recording and/or collecting user biometric information without any additional action from the user. Embodiments of the present invention improve the art of biometric data by enabling the collection of biometric information from the user when the user doesn't have a biometric capable device. Additionally, embodiments of the present invention can understand user's biometric information to better serve the user, and understand user's change of biometric information and leverage that information to better serve the user.

Biometric identifiers are then distinctive, measurable characteristics used to label and describe individuals. Biometric identifiers are often categorized as physiological versus behavioral characteristics. Physiological characteristics are related to the shape of the body. Examples include, but are not limited to fingerprint, palm veins, face recognition, DNA, palm print, hand geometry, iris recognition, retina and odor/scent. Behavioral characteristics are related to the pattern of behavior of a person, including but not limited to typing rhythm, gait, and voice. Biometric identifiers can often be used as biomarkers indicative of a presence of disease/infection or specific environmental exposure.

It should be noted that biometric identifier(s) and/or biometric data are interchangeable and synonymous with one another. Additionally, it should be noted that biometric identifier(s) and/or data are interchangeable and/or synonymous with biomarker identifier(s) and/or biomarker data throughout the entire specification.

Implementation of embodiments of the invention may take a variety of forms, and exemplary implementation details are discussed subsequently with reference to the Figures.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It can also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations can be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

FIG. 1 is a functional block diagram illustrating a distributed data processing environment, generally designated 100, in accordance with one embodiment of the present invention. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes mobile device 110, server computer 120, interconnected over network 130. Network 130 can be, for example, a telecommunications network, a local area network (LAN), a wide area network (WAN), such as the Internet, or a combination of the three, and can include wired, wireless, or fiber optic connections. Network 130 can include one or more wired and/or wireless networks that are capable of receiving and transmitting data, voice, and/or video signals, including multimedia signals that include voice, data, and video information. In general, network 130 can be any combination of connections and protocols that will support communications between mobile device 110 and server computer 120, and other computing devices (not shown in FIG. 1) within distributed data processing environment 100.

In various embodiments, mobile device 110 can be, but is not limited to, a standalone device, a server, a laptop computer, a tablet computer, a netbook computer, a personal computer (PC), a smart phone, a desktop computer, a smart television, a smart watch, a wearable fitness device, a biometric device, and/or any programmable electronic computing device capable of communicating with various components and devices within distributed data processing environment 100, via network 130 or any combination therein. In general, mobile device 110 are representative of any programmable mobile device or a combination of programmable mobile devices capable of executing machine-readable program instructions and communicating with users of other mobile devices via network 130 and/or capable of executing machine-readable program instructions and communicating with server computer 120. In other embodiments, mobile device 110 can represent any programmable electronic computing device or combination of programmable electronic computing devices capable of executing machine readable program instructions, manipulating executable machine readable instructions, and communicating with server computer 120 and other computing devices (not shown) within distributed data processing environment 100 via a network, such as network 130. Mobile device 110 includes an instance of user interface 106. Mobile device 110 and user interface 106 allow a user to interact with biomarker identifier component (BIC) 122 in various ways, such as sending program instructions, receiving messages, sending data, inputting data, editing data, correcting data and/or receiving data.

User interface (UI) 106 provides an interface to biomarker identifier component 122 on server computer 120 for a user of mobile device 110. In one embodiment, UI 106 can be a graphical user interface (GUI) or a web user interface (WUI) and can display text, documents, web browser windows, user options, application interfaces, and instructions for operation, and include the information (such as graphic, text, and sound) that a program presents to a user and the control sequences the user employs to control the program. In another embodiment, UI 106 can also be mobile application software that provides an interface between a user of mobile device 110 and server computer 120. Mobile application software, or an "app," is a computer program designed to run on smart phones, tablet computers and other mobile devices. In an embodiment, UI 106 enables the user of mobile device 110 to send data, input data, edit data, correct data and/or receive data. In various embodiments, UI 106 can enable the user to upload/enter user biomarker and/or user biometric identifiers to biomarker identifier component 122 for analysis and/or cognitive learning.

Server computer 120 can be a standalone computing device, a management server, a web server, a mobile computing device, or any other electronic device or computing system capable of receiving, sending, and processing data.

In other embodiments, server computer 120 can represent a server computing system utilizing multiple computers as a server system, such as in a cloud computing environment. In another embodiment, server computer 120 can be a laptop computer, a tablet computer, a netbook computer, a personal computer (PC), a desktop computer, a personal digital assistant (PDA), a smart phone, or any other programmable electronic device capable of communicating with mobile device 110 and other computing devices (not shown) within distributed data processing environment 100 via network 130. In another embodiment, server computer 120 represents a computing system utilizing clustered computers and components (e.g., database server computers, application server computers, etc.) that act as a single pool of seamless resources when accessed within distributed data processing environment 100. Server computer 120 can include biomarker identifier component 122 and shared storage 124. Server computer 120 can include internal and external hardware components, as depicted, and described in further detail with respect to FIG. 4.

Shared storage 124 and local storage 108 can be a data repository and/or a database that can be written to and/or read by one or a combination of biomarker identifier component 122, server computer 120 and/or computing devices 110. In the depicted embodiment, shared storage 124 resides on server computer 120. In another embodiment, shared storage 124 can reside elsewhere within distributed data processing environment 100 provided coverage assessment program 110 has access to shared storage 124. A database is an organized collection of data. Shared storage 124 and/or local storage 108 can be implemented with any type of storage device capable of storing data and configuration files that can be accessed and utilized by server computer 120, such as a database server, a hard disk drive, or a flash memory. In other embodiments, shared storage 124 and/or local storage can be hard drives, memory cards, computer output to laser disc (cold storage), and/or any form of data storage known in the art. In various embodiments, biomarker identifier component 122 can store and/or retrieve data from shared storage 124 and/or local storage 108. For example, biomarker identifier component 122 stores biometric data to shared storage 124 to be retrieved later and used as a reference and/or element of analysis.

In various embodiments, biomarker identifier component 122 can create a user profile and store the user profile data on local storage 122 and/or shared storage 124. Additionally, in various embodiments, biomarker identifier component 122 can have cognitive capabilities and learn from previously save/stored data, and/or any data that biomarker identifier component 122 has interacted with previously. For example, retrieving and analyze a user's previously documented to determine the most efficient method of repair. Biometric identifiers and/or biometric data can be, but is not limited to, age, gender, heritage, language, medical history, height, weight, body mass index (BMI) geographical region, nationality, general medical knowledge/information, blood pressure, heart rate, calories burned and/or calories consumed, steps taken, miles walked, steps ran/jogged, distance ran, steps taken, oxygen levels, glucose level, blood pH level, salinity of user perspiration, perspiration level, behavioral health history, dopamine level, brain activity, and/or body temperature. In some embodiments, biometric data can include user data/personal data. Biomarker identifier can be, but is not limited to, current mood, historic mood, type of music associated with mood, behavior (music selection, skipping songs, fast-forwarding, repeating songs, intensity of a workout, etc.), music selection (e.g., music selection, genera of music, tone, rhythm, pitch, volume, etc.), facial expressions, and/or user biometric identifiers responding to music selection (change in heart rate, change in pulse, amount of perspiration, change in breaths per minute, change in dopamine level, etc.).

In the exemplary embodiment, biomarker identifier component 122 is housed on server computer 120; however, in other embodiments, biomarker identifier component 122 can be housed on mobile device 110, and/or a computing device and/or server computer not depicted in FIG. 1. In various embodiments, biomarker identifier component 122 can link to a biometric capable device and monitor and/or record (e.g., a recording module) biometric data. For example, a user wears the biometric capable device (i.e., Smart Watch) and plays music, biomarker identifier component 122 collects user's location/region the user's age, gender and biometric information, Music played with satisfaction, and time window (e.g., a predetermined time interval, range, and/or duration of a song played).

In various embodiments, biomarker identifier component 122 can utilize the biometric data and/or biomarker identities collected/recorded by and/or entered into a biometric capable device, biometric capable mobile application, biometric data website, and/or mobile music application to create a user biometric profile. For example, linking to a mobile music application and/or a fitness application, receiving the user's current audio preference, in this particular example it's Hip-hop, then retrieving and comparing the user's historic audio preferences and historic biometric data to the user's current audio preferences and audio preferences. Furthermore, in this particular example, biomarker identifier component 122 creates a user biometric profile based on the analysis of the user's current and historic audio preferences and biometric data, and outputs the profile to the user and/or medical professional. In various embodiments, biomarker identifier component 122 can have a learning phase, in which biomarker identifier component 122 monitors and/or records a user's biometric data, biomarker identifiers, and/or audio preferences. Audio preferences can be, but are not limited to, genre, music artist, lyrics, volume music is played, frequency of songs played (e.g., frequently played songs), custom playlists, saved songs, liked songs, disliked songs, and/or songs skipped. In various embodiments, biomarker identifier component 122 can retrieve audio preferences form a music application (e.g., mobile music application). In various embodiments, audio preferences can comprise music attributes (e.g., subjective music attributes and/or objective music attributes).

In various embodiments, biomarker identifier component 122 can, crowd source biometric data, behavioral data, and/or biomarker identifiers and record them accordingly. In various embodiments, biomarker identifier component 122 can integrate with a cloud based cognitive system, artificial intelligent computer system, and/or management system. In various embodiments, biomarker identifier component 122 can utilize the location information from mobile device 110 (e.g., global positioning system (gps) tracking and/or location information). Additionally, in various embodiments, biomarker identifier component 122 can access a user's mobile applications and/or website profile and retrieve biometric data. For example, a user's age, gender, location, location history, preferences, and/or occupation from a music streaming website and/or mobile application, and/or from social media websites and/or mobile applications.

In various embodiments, biomarker identifier component 122 can use a cloud based service to collect biometric data, behavioral data, and/or biomarker identifiers and cognitively learn a user's musical preferences, behavioral data (e.g., how certain songs effect a user's mood, and/or how the user's mood effects song selection/song choice). For example, monitoring and recording if the user has fast forwarded the music versus if the user has fully listened to the music or even repetitively played the music or "liked" the music. In various embodiments, music played with satisfaction can be determined by monitoring and/or recording user behavior and audio preference.

In various embodiments, biomarker identifier component 122 can collect biometric data and/or biomarker identifiers when a user is not wearing a biometric capable device. For example, a user listening to music in a car while driving, via Bluetooth connection to the user's smartphone, biomarker identifier component 122 can collect the user's location/region, age, gender, music played with satisfaction (e.g., duration of each song played, type of songs skipped, music genre, etc.), and time window. In various embodiments, biomarker identifier component 122 examines the music played during the time the user isn't wearing a biometric capable device and determines the associated biometric information by sourcing information/data from the recorded/historic data of when the user was wearing a biometric capable device. In various embodiments, when there is enough data collected from when a user is wearing a biometric device, the accuracy of the sourcing can be further improved by matching user's gender, age window, and/or even location/region.

In various embodiments, biomarker identifier component 122 can identify biomarker change indicators for behavioral health, by: monitoring and/or recording music choices, extracting the attributes of the music choices, model the attributes of the music choices against historic biomarker data, and alert a user to one or more changes to the biomarker change indicators and/or biometric data. In various embodiments, biomarker identifier component 122 can split the music selection into segments (e.g., 1 sec, 10 sec), key changes, time changes, and/or latent/background audio and accumulate a score over a predetermined time-period/interval before alerting a user and/or medical professional. In various embodiments, the accumulated score can be a predetermined threshold set by the user, legal guardian, and/or medical professional. In various embodiments, the music segments can be predetermined. In some embodiments, the alert can in the form of a text, a phone call, an email, a social media post, a push notification, shutting down the mobile music application, playing a voice recording, one or more vibrations, one or more sounds, and/or any other form of notification methods known in the art. In other embodiments, biomarker identifier component 122 can output one or more alerts. In some embodiments, the alert system can be incremental and increase with intensity based on a predetermined threshold.

In various embodiments, the accumulated score based on current and historic user biometric data and/or biomarker identifiers can be used to develop cohort models as indicators of behavioral health, use the alert as an approximate, exact or relative effect, and/or isolate the music based on region or demographic background (e.g., age, gender, region) or medical background. In various embodiments, biomarker identifier component 122 monitors, records, and/or analyzes the quality of music by parsing the music into subjective music attributes and objective music attributes, in which the subjective music attributes and objective music attributes can be used for analysis. Subjective music attributes comprises: Tonal character (usually pitched), noisy, with or without some tonal character, including rustle noise, coloration, beginning, ending, coloration glide or formant glide, micro-intonation, microtonality, vibrato, tremolo, attack, final sound, and/or any other subjective music attribute known in the art. Objective music attributes comprise: periodic sound, noise (e.g., random pulses characterized by the rustle time, the mean interval between pulses), spectral envelope, physical rise and decay time, change of spectral envelope, change in frequency (e.g., a predetermined variable of change such as one up and/or one down), frequency modulation, amplitude modulation, music prefix, music suffix and/or any other objective music attribute known in the art. In various embodiments, biomarker identifier component 122 can extract the object qualities of the music through conversion to a mathematical model and time function.

In various embodiments, biomarker identifier component 122 can source the subjective music attributes through personal survey or crowdsourced evaluation of the music. For example, a user loads/opens a music application on a smartphone and begins listening to music using the music application while on train. In this particular example, biomarker identifier component 122 triggers the monitoring the music choice and biomarker identifier component 122 begins to extract the frequency and/or amplitude of the music selected and/or played. In this particular example, biomarker identifier component 122 models the qualities of the music choices as a continuous function. Furthermore, in this particular example, biomarker identifier component 122 compares the choices against historic biomarkers as associated with prior health indicators, and determines the user's mood has dropped below a predetermined threshold and alerts the user. In other embodiments, biomarker identifier component 122 can alert the user, a healthcare professional, and/or any other authorized member.

In various embodiments, biomarker identifier component 122 can monitor and/or record user music choices. In various embodiments, biomarker identifier component 122 can monitor music choices utilizing a shim, which intercepts the audio, records the music title, artist, start time, and end time (and fingerprint of the music), and captures a continuous feed of the background audio. In other embodiments, biomarker identifier component 122 can monitor and/or record user music choices by also capturing a user's location/region, user's age, user's gender, music played with satisfaction, time window, and action/response to the music (e.g., fast-forwarding, skipping, repeating, etc.).

Figure 2:
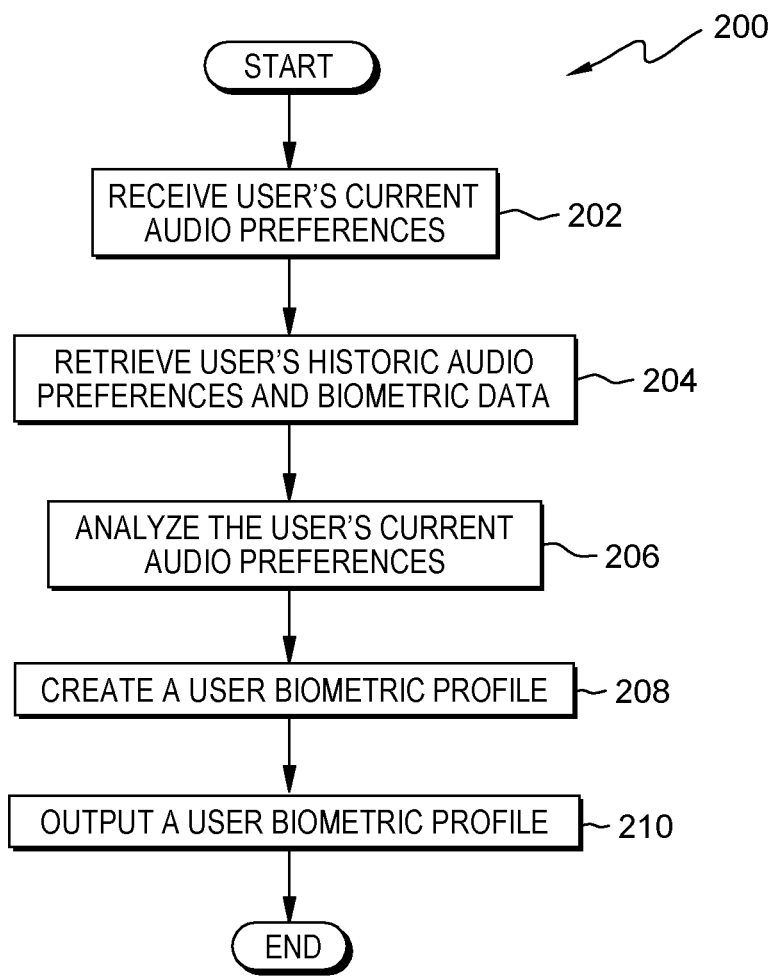
FIG. 2 illustrates operational steps of biomarker identifier component, on a server computer within the distributed data processing environment of FIG. 1, in accordance with an embodiment of the present invention.

FIG. 2 is a flowchart depiction operational steps of biomarker identifier component 122, generally designated 200, on server computer 120 within distributed data processing environment 100 of FIG. 1, monitoring biometric and biomarker data, in accordance with an embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

In step 202, biomarker identifier component 122 receives a user's current audio preferences. In various embodiments, biomarker identifier component 122 can receive one or more user preferences from a music application (e.g., mobile music application). In various embodiments, biomarker identifier component 122 can receive a user's audio preferences in real-time.

In step 204, biomarker identifier component 122 retrieves a user's historic audio preferences and biometric data. In various embodiments, biomarker identifier component 122 can retrieve a user's historic audio preferences, historic biometric data, and/or real-time biometric data from local storage 108 and/or shared storage 124.

In step 206, biomarker identifier component 122 analyzes the user's current audio preferences. In various embodiments, biomarker identifier component 122 can analyze the user's current audio preferences and compare them against the user's historic audio preferences, historic biometric data, and current biometric data. In various embodiments, biomarker identifier component 122 can determine how audio preferences affects a user's biometric data and/or biomarker data and viscera.

In step 208, biomarker identifier component 122 creates a user biometric profile. In various embodiments, biomarker identifier component 122 creates a user biometric profile based on current audio preferences, historic audio preferences, current biometric data, and/or historic biometric data.

In step 210, biomarker identifier component 122 outputs a user biometric profile. In various embodiments, biomarker identifier component 122 outputs a user biometric profile based on the analysis of historic and current biometric data and/or audio preferences.

Figure 3:
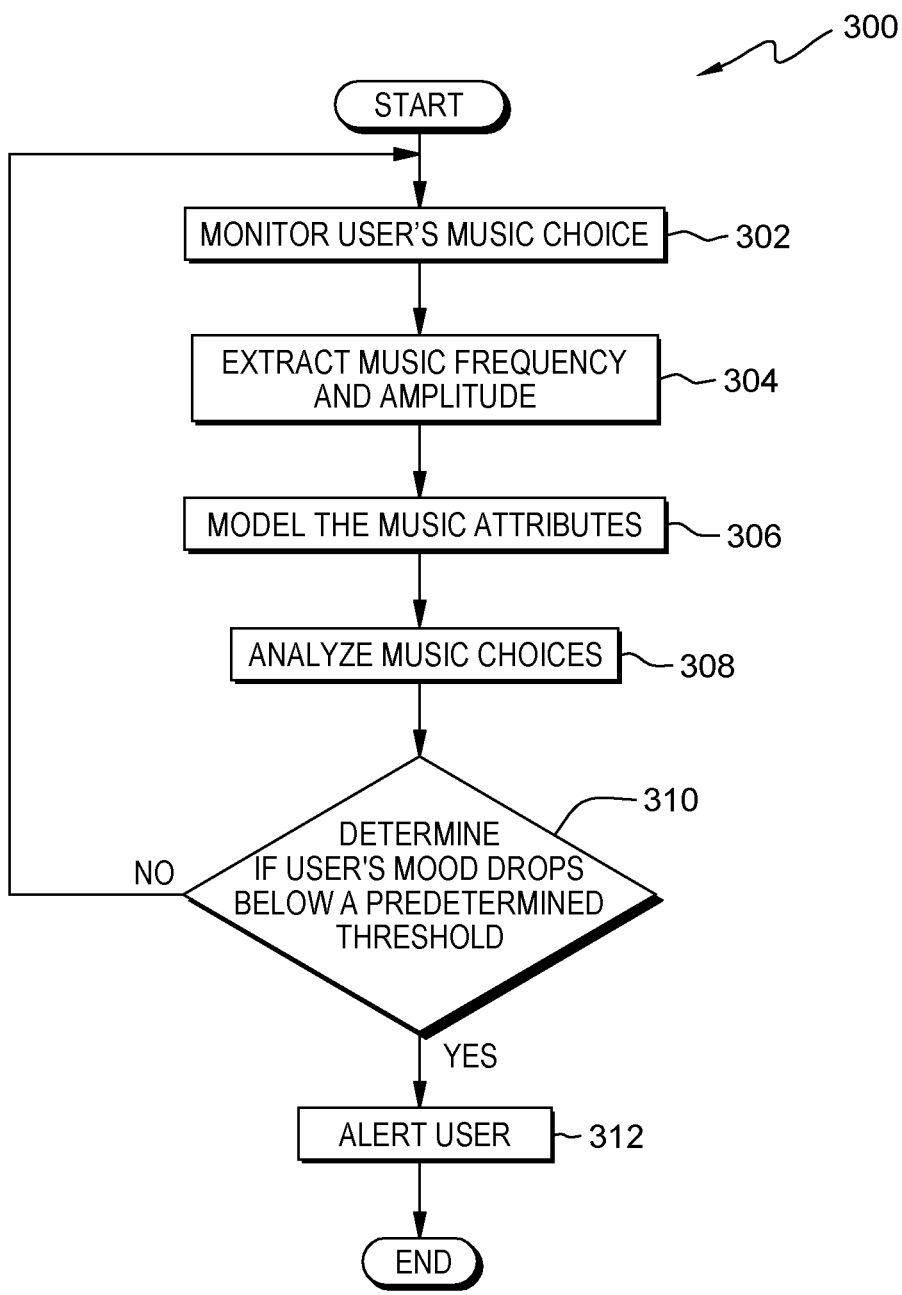
FIG. 3 illustrates operational steps of biomarker identifier component, on a server computer within the distributed data processing environment of FIG. 1, in accordance with an embodiment of the present invention.

FIG. 3 is a flowchart depiction operational steps of biomarker identifier component 122, generally designated 300, on server computer 120 within distributed data processing environment 100 of FIG. 1, monitoring biometric and biomarker data, in accordance with an embodiment of the present invention. FIG. 3 provides only an illustration of one implementation and does not imply any limitations with regard to the environments in which different embodiments may be implemented. Many modifications to the depicted environment may be made by those skilled in the art without departing from the scope of the invention as recited by the claims.

In step 302, biomarker identifier component 122 monitors a user's music choice. In various embodiments, biomarker identifier component 122 monitors a user's music choice and/or audio preferences. In various embodiments, biomarker identifier component 122 can retrieve and/or monitor a user's music choice and/or audio preferences from the user's biometric profile.

In step 304, biomarker identifier component 122 extracts the music frequency and amplitude. In various embodiments, biomarker identifier component 122 can extract the music frequency and amplitude from the user's biometric profile and/or current music choice.

In step 306, biomarker identifier component 122 models the music attributes. In various embodiments, biomarker identifier component 122 can generate one or more models based on audio preferences, subjective music attributes and/or objective attributes.

In step 308, biomarker identifier component 122 analyzes music choice. In various embodiments, biomarker identifier component 122 can analyze a user's music choice, extracted music frequency and amplitude, the one or more models, historic biometric data, current biometric data, historic audio preferences, current audio preferences, and/or user music choice. In various embodiments, biomarker identifier component 122 can accumulate a score over a predetermined time period.

In step 310, biomarker identifier component 122 determines if the user's mood drops below a predetermined threshold. In various embodiments, biomarker identifier component 122 can determine if the user's mood drops below a predetermined threshold based on the analysis in step 308. In this particular embodiment, if biomarker identifier component 122 determines the user's mood drops below the predetermined threshold (Yes branch) then biomarker identifier component 122 will advance to step 312; however, if biomarker identifier component 122 determines that the users mood hasn't dropped below the predetermined threshold (No branch), then biomarker identifier component 122 will repeat steps 302 through 310 until biomarker identifier component 122 determines the user's mood drops below the predetermined threshold. In various embodiments, the predetermined threshold can be incremental, wherein the predetermined threshold includes levels/varying degrees of intensity and/or seriousness and/or warning thresholds.

In step 312, biomarker identifier component 122 alerts the user. In various embodiments, responsive to determining if the user's mood drops below the predetermined threshold, biomarker identifier component 122 can alert the user of the user's change in biomarker indicators/mood. In various embodiments, the alerts can be incremental starting with warning alerts if the user approaches the predetermined threshold within a predetermine buffer zone and the alerts intensify as the users accumulate score reaches closer to the threshold.

Figure 4:
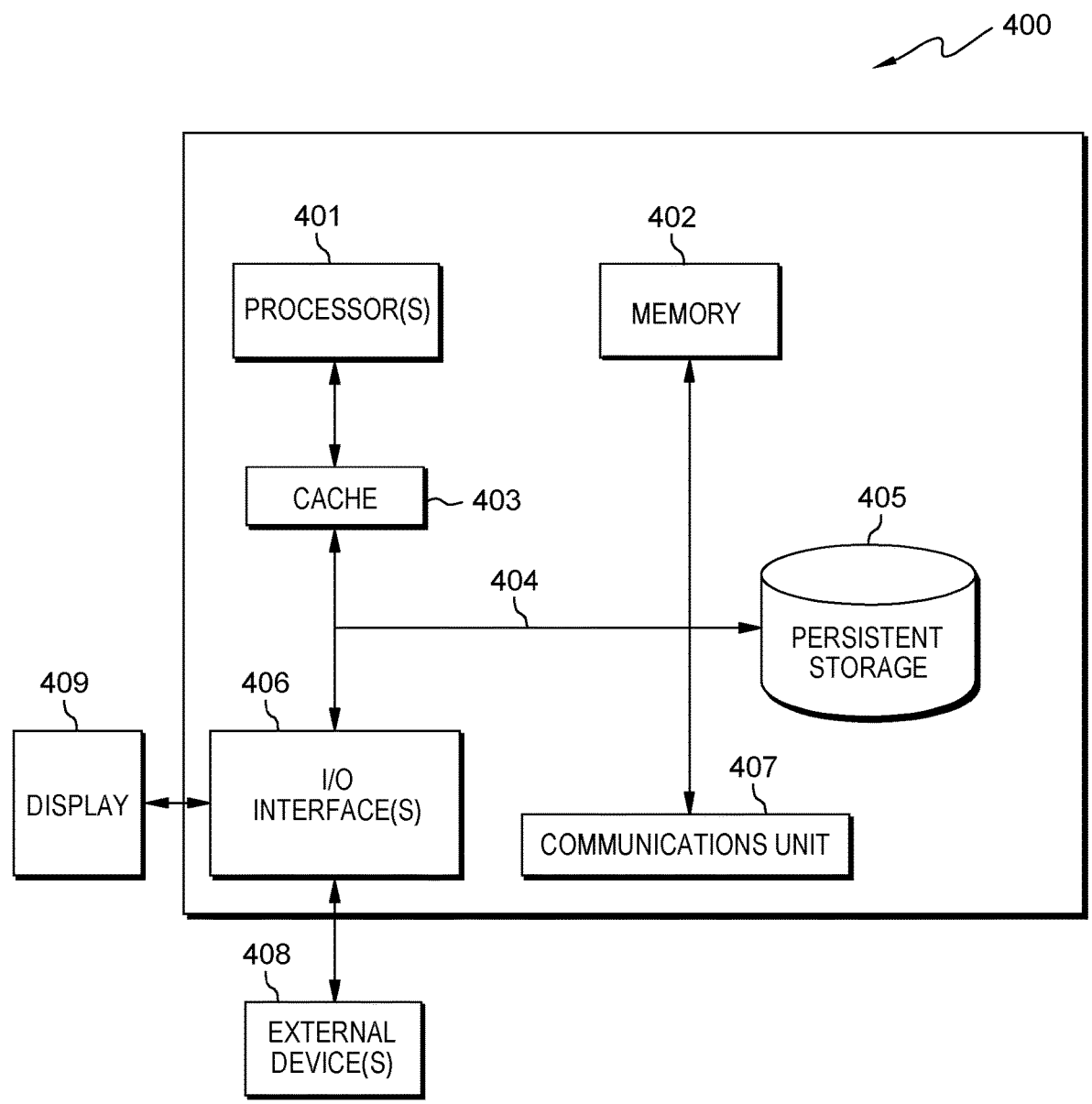
FIG. 4 depicts a block diagram of components of the server computer executing the calibration component within the distributed data processing environment of FIG. 1, in accordance with an embodiment of the present invention.

FIG. 4 depicts a block diagram of components of server computer 120 within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

FIG. 4 depicts a block diagram of components of a computing device within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

FIG. 4 depicts computer system 400, where server computer 120 represents an example of computer system 400 that includes biomarker identifier component 122. The computer system includes processors 401, cache 403, memory 402, persistent storage 405, communications unit 407, input/output (I/O) interface(s) 406 and communications fabric 404. Communications fabric 404 provides communications between cache 403, memory 402, persistent storage 405, communications unit 407, and input/output (I/O) interface(s) 406. Communications fabric 404 can be implemented with any architecture designed for passing data and/or control information between processors (such as microprocessors, communications and network processors, etc.), system memory, peripheral devices, and any other hardware components within a system. For example, communications fabric 404 can be implemented with one or more buses or a crossbar switch.

Memory 402 and persistent storage 405 are computer readable storage media. In this embodiment, memory 402 includes random access memory (RAM). In general, memory 402 can include any suitable volatile or non-volatile computer readable storage media. Cache 403 is a fast memory that enhances the performance of processors 401 by holding recently accessed data, and data near recently accessed data, from memory 402.

Program instructions and data used to practice embodiments of the present invention may be stored in persistent storage 405 and in memory 402 for execution by one or more of the respective processors 401 via cache 403. In an embodiment, persistent storage 405 includes a magnetic hard disk drive. Alternatively, or in addition to a magnetic hard disk drive, persistent storage 405 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 405 may also be removable. For example, a removable hard drive may be used for persistent storage 405. Other examples include optical and magnetic disks, thumb drives, and smart cards that are inserted into a drive for transfer onto another computer readable storage medium that is also part of persistent storage 405.

Communications unit 407, in these examples, provides for communications with other data processing systems or devices. In these examples, communications unit 407 includes one or more network interface cards. Communications unit 407 may provide communications through the use of either or both physical and wireless communications links. Program instructions and data used to practice embodiments of the present invention may be downloaded to persistent storage 405 through communications unit 407.

I/O interface(s) 406 enables for input and output of data with other devices that may be connected to each computer system. For example, I/O interface 406 may provide a connection to external devices 408 such as a keyboard, keypad, a touch screen, and/or some other suitable input device. External devices 408 can also include portable computer readable storage media such as, for example, thumb drives, portable optical or magnetic disks, and memory cards. Software and data used to practice embodiments of the present invention can be stored on such portable computer readable storage media and can be loaded onto persistent storage 405 via I/O interface(s) 406. I/O interface(s) 406 also connect to display 409.

Display 409 provides a mechanism to display data to a user and may be, for example, a computer monitor.

What is claimed is:

1. A method for detecting user biomarker identifier changes based on audio preferences and generating biometric alerts based on the detected user biomarker identifier changes, the method comprising:
    receiving, by one or more processors, a user's current audio preferences;
    retrieving, by the one or more processors, user's historic audio preferences and biometric data associated with the user's historic audio preferences;
    analyzing, by the one or more processors, the user's current audio preferences based on the user's historic audio preferences and the biometric data associated with the user's historic audio preferences;
    creating, by the one or more processors, a user biometric profile based on analyzing the user's current audio preferences, the user's historic audio preferences and the biometric data associated with the user's historic audio preferences; and
    outputting, by the one or more processors, the user biometric profile;
    accumulating, by the one or more processors, a score based on historic biomarker identifiers stored in the user biometric profile, current biomarker identifiers over a predetermined time-period, current user biometric data and the biometric data associated with the user's historic audio preferences wherein the accumulated score develops models as indicators of behavioral health, and isolates music from the accumulated score based on region, demographic background and medical background.

2. The method of claim 1, wherein said analyzing the user's current audio preferences further comprises:
    parsing, by the one or more processors, the user's current audio preferences into subjective music attributes and objective music attributes.

3. The method of claim 2, wherein the subjective music attributes comprise: tonal character, noisy, with or without some tonal character, including rustle noise, coloration, beginning, ending, coloration glide or formant glide, microintonation, microtonality, vibrato, tremolo, attack, and final sound.

4. The method of claim 2, wherein the objective music attributes comprise: periodic sound, noise, spectral envelope, physical rise and decay time, change of spectral envelope, change in frequency, frequency modulation, amplitude modulation, music prefix, and music suffix.

5. The method of claim 1, wherein the user's current audio preferences are divided into time segments of a predetermined interval.

6. The method of claim 1, further comprising:
    alerting, by the one or more processors, health professionals associated with a user based on the user biometric profile, wherein said alerting is incremental starting with warning alerts if the user approaches a predetermined threshold within a predetermine buffer zone, wherein the warning alerts intensify as the user accumulated the score that reaches closer to the predetermined threshold.

7. The method of claim 1, wherein the user's current audio preferences comprise at least one of: genre, music artist, lyrics, volume music is played, frequency of songs played, custom playlists, saved songs, liked songs, disliked songs, songs skipped, or background audio.

* * * * *